United States Patent
Bogart

(10) Patent No.: US 6,664,292 B2
(45) Date of Patent: Dec. 16, 2003

(54) METHODS FOR THE TREATMENT OF NAIL FUNGUS AND OTHER MICROBIAL AND MYCOTIC CONDITIONS AND COMPOSITIONS USEFUL THEREFOR

(76) Inventor: Mark H. Bogart, 3631 Woodlawn Terrace Pl., Honolulu, HI (US) 96822-1474

(*) Notice: Subject to any disclaimer, the term of this patent is extended or adjusted under 35 U.S.C. 154(b) by 0 days.

(21) Appl. No.: 09/873,773

(22) Filed: Jun. 4, 2001

(65) Prior Publication Data

US 2002/0183387 A1 Dec. 5, 2002

(51) Int. Cl.$^7$ .................. A61K 31/19; A61K 31/045
(52) U.S. Cl. ............... 514/557; 514/858; 514/724
(58) Field of Search .................. 514/557, 858, 514/724

(56) References Cited

U.S. PATENT DOCUMENTS

| | | | |
|---|---|---|---|
| 2,970,032 A | * 1/1961 | Jekel | |
| 4,180,058 A | 12/1979 | Brem | 128/1 |
| 4,975,217 A | * 12/1990 | Brown-Skrobot et al. | 514/574 |
| 4,986,963 A | * 1/1991 | Corcoran et al. | 422/30 |
| 5,043,357 A | * 8/1991 | Hoffler et al. | 514/553 |
| 5,145,663 A | * 9/1992 | Simmons | 424/47 |
| 5,391,367 A | 2/1995 | DeVincentis et al. | 424/61 |
| 5,422,366 A | 6/1995 | Mintzis et al. | 514/474 |
| 5,519,059 A | 5/1996 | Sawaya | 514/599 |
| 5,525,635 A | 6/1996 | Moberg | 514/588 |
| 5,613,538 A | * 3/1997 | Brisson | 144/228 |
| 5,641,475 A | * 6/1997 | Yu et al. | 424/65 |
| 5,652,256 A | 7/1997 | Knowles | 514/399 |
| 5,807,890 A | * 9/1998 | Yu et al. | 514/574 |
| 5,814,305 A | 9/1998 | Laugier et al. | 424/61 |
| 5,853,767 A | 12/1998 | Melman | 424/659 |
| 5,889,039 A | 3/1999 | Knowles | 514/399 |
| 5,916,545 A | 6/1999 | Burnett et al. | 424/61 |
| 5,968,986 A | * 10/1999 | Dyer | 514/643 |
| 5,993,790 A | 11/1999 | Strauss | 424/61 |
| 6,066,670 A | * 5/2000 | Brown | 514/557 |
| 6,231,840 B1 | 5/2001 | Buck | 424/61 |
| 2001/0025058 A1 | * 9/2001 | Borowy-Borowski et al. | |
| 2002/0004057 A1 | * 1/2002 | Tabasso | 424/405 |

FOREIGN PATENT DOCUMENTS

| | | | |
|---|---|---|---|
| WO | WO96/36311 | * | 11/1996 |
| WO | WO01/12173 | * | 2/2001 |

OTHER PUBLICATIONS

Scott, W. Antifungal agent, Database IPA, AN:71:194, abstract, Hospital pharmacy, 1971, vol.6, pp. 17–20.*

* cited by examiner

Primary Examiner—Kevin E. Weddington
Assistant Examiner—Vickie Kim
(74) Attorney, Agent, or Firm—Stephen E. Reiter; Foley & Reiter

(57) ABSTRACT

In accordance with the present invention, there are provided methods for treatment of pathological conditions of the nail, said method comprising topically applying to the affected area an effective amount of a composition comprising an optionally substituted lower alcohol and an optionally substituted lower carboxylic acid. Invention methods effectively treat bacterial or fungal infections of the nail by utilizing a low viscosity composition having the ability to penetrate through and underneath the nail plate, thereby attacking the infection at its source.

14 Claims, No Drawings

METHODS FOR THE TREATMENT OF NAIL FUNGUS AND OTHER MICROBIAL AND MYCOTIC CONDITIONS AND COMPOSITIONS USEFUL THEREFOR

FIELD OF THE INVENTION

The present invention relates to methods for treating pathological conditions of the nail and compositions useful therefor. In a particular aspect, the invention relates to methods for treating conditions resulting from bacterial or fungal infections of the nail, and compositions useful therefor.

BACKGROUND OF THE INVENTION

In the field of dermatology, topical administration of pharmaceutically active agents has often been employed for treating pathological conditions. Many of the concerns associated with other types of administration can often be avoided by topically administering an active agent to a subject in need thereof. For example, reliable delivery of a pharmaceutically active agent to organs or tissues in need thereof via oral administration is often difficult due to variable rates of absorption and metabolism associated with oral delivery. In contrast, topical administration of a pharmaceutically active agent can provide high doses of the active agent directly to the infected area, and often minimizes side effects.

Although maladies of the skin can often be effectively treated by topical administration of pharmaceutically active agents, successful treatment of conditions of the nail has remained elusive. Due to the hyperkeratotic nature of the nail, pharmaceutical formulations in the form of creams, gels, and lotions are unable to penetrate the nail plate. Thus, it has proven quite difficult to effectively deliver a pharmaceutically active agent into and beneath the nail plate, where the cause of the pathological condition originates.

A particular condition of the nail which remains ineffectively treated is onychomycosis. This condition is a fungal infection of the nail most frequently caused by dermatophytes and molds. Indeed, onychomycosis refers to any dermatophyte infection of the nail plate and includes infection of nails by any fungus, such as yeast, molds, and the like. Onychomycosis results in a discoloration of the finger nails and toe nails which is often accompanied by pain when pressure is applied to the infected nail.

A number of attempts have been made to effectively treat nail fungus, each meeting with limited success. For example, surgical removal of the nail or drilling holes in the nail to allow penetration of anti-fungal topical treatments results in considerable patient discomfort; systemic administration of anti-fungal drugs suffers from the inherent difficulties involved with parenteral administration and may also result in undesirable side-effects; and anti-fungal lacquers (painted on the nail) lack the necessary penetrating power to directly reach the fungal infection.

Accordingly, there remains a need for effective treatment of pathological conditions of the nail.

BRIEF DESCRIPTION OF THE INVENTION

In accordance with the present invention, there are provided methods for treatment of pathological conditions of the nail. Invention methods comprise topically applying to the affected area an effective amount of a composition comprising an optionally substituted lower alcohol and an optionally substituted lower carboxylic acid. Invention methods effectively treat bacterial or fungal infections of the nail by utilizing a low viscosity composition having the ability to penetrate through and underneath the nail plate, thereby attacking the infection at its source.

Further provided by the present invention are compositions consisting essentially of an optionally substituted lower alcohol and an optionally substituted lower carboxylic acid. Invention compositions kill on contact all types of microbes, including fungi and bacteria. Thus, these compositions are extremely effective in combating pathological conditions of the nail, such as, for example, onychomycosis.

DETAILED DESCRIPTION OF THE INVENTION

In accordance with the present invention, there are provided methods and compositions useful for treatment of pathological conditions of the nail. Invention methods comprise topically applying to the affected area an effective amount of a composition comprising an optionally substituted lower alcohol and an optionally substituted lower carboxylic acid. Invention methods are particularly effective in treating conditions caused by microbial infections, such as fungal or bacterial infections.

Compositions employed by invention methods have an inherently low viscosity, thereby rendering the compositions particularly useful for treating infections of the nail. The low viscosity of invention compositions allows for enhanced penetration through and under the nail for prevention and treatment of infections. Particular infections which are effectively treated by invention methods and compositions include fungal infections, such, for example, onychomycosis.

Alcohols contemplated for use in the practice of the present invention include optionally substituted methanol, ethanol, propanol, butanol, and the like. Carboxylic acids contemplated for use in the practice of the present invention include formic acid or optionally substituted acetic acid, propionic acid, butyric acid, pentanoic acid, and the like. When compounds contemplated for use in the practice of the present invention are substituted, substituents include —OH, alkyl, substituted alkyl, alkenyl, substituted alkenyl, aryl, substituted aryl, alkoxy, substituted alkoxy, halogen (e.g., F, Cl, Br, I), $NO_2$, cyano, amino, carboxyl, amido, sulfuryl, —C(O)H, and the like.

As employed herein, "alkyl" refers to alkyl groups having up to about 6 carbon atoms, and "substituted alkyl" refers to alkyl groups bearing one or more substituents selected from hydroxy, alkoxy, halogen (e.g., F, Cl, Br, I), $NO_2$, cyano, amino, carboxyl, amido, sulfuryl, —C(O)H, and the like.

As employed herein, "alkenyl" refers to straight or branched chain hydrocarbyl groups having at least one carbon-carbon double bond, and having in the range of about 2 up to about 6 carbon atoms, and "substituted alkenyl" refers to alkenyl groups further bearing one or more substituents as set forth in the definition of "alkyl".

As employed herein, "aryl" refers to aromatic rings having up to about 10 carbon atoms, and "substitituted aryl" refers to aryl groups further bearing one or more substituents as set forth in the definition of "alkyl".

As employed herein, "alkoxy" refers to a group —OR, wherein R is an alkyl group as defined above.

Preferred alcohols contemplated for use in the practice of the present invention include methanol and ethanol. Presently most preferred alcohols contemplated for use in the practice of the present invention include optionally substituted methanols. Preferred carboxylic acids contemplated for use in the practice of the present invention include optionally substituted acetic acid and propionic acid. Presently most preferred carboxylic acids contemplated for use in the practice of the present invention include optionally substituted acetic acids.

Invention compositions typically comprise from about 50 wt % to about 90 wt % alcohol and about 10 wt % to about 40 wt % carboxylic acid. Preferred compositions comprise about 75 wt % alcohol and about 25 wt % carboxylic acid.

Invention compositions are readily prepared by mixing the desired alcohol with the desired carboxylic acid at room temperature to provide a low viscosity, homogeneous solution. Since the components of invention compositions are low molecular weight compounds, the resulting solutions are often volatile. Accordingly, the solutions should be stored in a suitable vessel, e.g., a septum-capped container, a tightly sealed screw-cap container, and the like. In addition, since invention compositions are quite stable, the compositions can be expected to have very long shelf lives.

The methods and compositions of the present invention are useful in the topical treatment of any bacterial, mycotic, or other microbial infection. Invention methods and compositions are particularly effective in treating infections that have not resulted in an open lesion. As employed herein, the term "microbial infections" refers to fungal infections as well as bacterial infections. Infections effectively treated by the methods and compositions of the present invention include any infections of the nail caused by a fungus, including yeasts and molds.

Invention compositions can be applied to the affected area in a variety of ways, e.g., by painting the nail, through use of a dropper, and the like. Invention compositions can be administered employing a variety of protocols, e.g., the compositions may be administered weekly until no sign of infection can be detected.

Further provided by the present invention are unit dosage forms comprising a container which holds therein an amount of a composition according to the present invention effective for topically treating a bacterial, mycotic, or other microbial infection. Unit dosage forms of the present invention further comprise an applicator for appropriate administration of invention compositions, as well as instructions for appropriate use of invention unit dosage forms.

The present invention provides several advantages over currently available treatment protocols for infections of the nail. In contrast to currently available topical treatments, the low viscosity of invention compositions allows for penetration through and under the nail, thereby killing fungus, including fungal spores, on contact. In addition, invention compositions have the ability to displace moisture present underneath the nail. Since moisture is a critical component of fungal growth, invention methods and compositions provide not only a cure for presently existing nail fungus, but also create an environment hostile to fungal growth, thereby preventing future infection. Indeed, this preventative component of the present invention provides the additional benefit of requiring only occasional administration, rather than the daily administration required by currently available nail lacquers. Moreover, invention methods greatly minimize patient discomfort, i.e., no surgical removal of the nail or drilling of the nail is required. Finally, the components of invention compositions are readily available and inexpensive, rendering the use of invention methods and compositions economically attractive.

While the invention has been described in detail with reference to certain preferred embodiments thereof, it will be understood that modifications and variations are within the spirit and scope of that which is described and claimed.

What is claimed is:

1. A method for treatment of a pathological condition of the nail, said method comprising topically applying to the affected area an effective amount of a composition consisting essentially of about 50 wt % to about 90 wt % of methanol and about 10 wt % to about 40 wt % of carboxylic acid having 1–5 carbons.

2. The method according to claim 1, wherein said pathological condition is microbial infection.

3. The method according to claim 2, wherein said microbial infection is fungal infection.

4. The method according to claim 3, wherein said fungal infection is onychomycosis.

5. The method according to claim 1, wherein said carboxylic acid having 1–5 carbons is formic acid, acetic acid, propionic acid, butyric acid, or pentanoic acid.

6. The method according to claim 5, wherein said carboxylic acid is acetic acid.

7. The method according to claim 6, wherein said composition consists essentially of about 50 wt % to about 90 wt % methanol and about 10 wt % to about 40 wt % acetic acid.

8. The method according to claim 7, wherein said composition consists essentially of about 75 wt % methanol and about 25 wt % acetic acid.

9. A method for treatment of fungal infection of the nail, said method comprising topically applying to the affected area an effective amount of a composition consisting essentially of about 50 wt % to about 90 wt % of an alcohol having 1–4 carbons and about 10 wt % to about 40 wt % of carboxylic acid having 1–5 carbons.

10. The method according to claim 9, wherein said fungal infection is onychomycosis.

11. The method according to claim 9, wherein said composition consists essentially of about 75 wt % alcohol and about 25 wt % carboxylic acid.

12. A method for the treatment of onychomycosis, said method comprising topically applying to the affected area an effective amount of a composition consisting essentially of about 75 wt % methanol and about 25 wt % acetic acid.

13. A method for treatment of a pathological condition of the nail, said method comprising topically applying to the affected area an effective amount of a composition consisting of about 50 wt % to about 90 wt % of methanol and about 10 wt % to about 40 wt % of carboxylic acid having 1–5 carbons.

14. A method for treatment of fungal infection of the nail, said method comprising topically applying to the affected area an effective amount of a composition consisting of about 50 wt % to about 90 wt % of an alcohol having 1–4 carbons and about 10 wt % to about 40 wt % of carboxylic acid having 1–5 carbons.

* * * * *